(12) United States Patent
Stiller et al.

(10) Patent No.: US 10,533,149 B2
(45) Date of Patent: Jan. 14, 2020

(54) TEMPERATURE CONTROL APPARATUS

(71) Applicant: XYLEM IP MANAGEMENT S.À R.L., Senningerberg (LU)

(72) Inventors: Wilfried Stiller, Holm (DE); Ulrich Lüdersen, Winsen/Luhe (DE); Eilert Balssen, Wedemark (DE)

(73) Assignee: XYLEM IP MANAGEMENT S.À R.L., Luxembourg (LU)

( * ) Notice: Subject to any disclaimer, the term of this patent is extended or adjusted under 35 U.S.C. 154(b) by 81 days.

(21) Appl. No.: 15/524,715

(22) PCT Filed: Oct. 22, 2015

(86) PCT No.: PCT/EP2015/074493
§ 371 (c)(1),
(2) Date: May 5, 2017

(87) PCT Pub. No.: WO2016/071118
PCT Pub. Date: May 12, 2016

(65) Prior Publication Data
US 2017/0335265 A1    Nov. 23, 2017

(30) Foreign Application Priority Data

Nov. 6, 2014 (DE) .......................... 10 2014 016 297

(51) Int. Cl.
*C12M 1/107* (2006.01)
*C12M 3/00* (2006.01)
(Continued)

(52) U.S. Cl.
CPC ............ *C12M 21/04* (2013.01); *C12M 23/46* (2013.01); *C12M 23/54* (2013.01); *C12M 27/02* (2013.01);
(Continued)

(58) Field of Classification Search
CPC ...... C12M 21/04; C12M 23/46; C12M 23/54; C12M 27/06; C12M 27/18; C12M 41/24; C12M 27/02; Y02E 50/343
See application file for complete search history.

(56) References Cited

FOREIGN PATENT DOCUMENTS

CA    1102019 A    5/1981
DE    2821790 A1    11/1979
(Continued)

OTHER PUBLICATIONS

International Preliminary Report on Patentability for International Application No. PCT/EP2015/074493, dated May 9, 2017, 9 pages.
(Continued)

*Primary Examiner* — Gautam Prakash
(74) *Attorney, Agent, or Firm* — RatnerPrestia

(57) ABSTRACT

A tempering device for tempering of biomass contained in a container, including at least one tempering mechanism, and at least one conveying device for conveying a mass flow of biomass in a main flow direction. The at least one conveying device includes at least one agitator, and wherein the at least one tempering mechanism is arranged in the main flow direction generated by the at least one conveying device. The at least one tempering mechanism is tubular with an inner tube and with an outer tube arranged coaxially to the inner tube. The inner tube and the outer tube form an intermediate space through which a tempering medium may flow. The tempering mechanism is oriented relative to the conveying device such that, in operation of the heating device, at least 40% of the delivery volume of the mass flow generated by the conveying device flows through the inner tube.

7 Claims, 4 Drawing Sheets

(51) Int. Cl.
*C12M 1/06* (2006.01)
*C12M 1/00* (2006.01)
*C12M 1/02* (2006.01)

(52) U.S. Cl.
CPC ............ *C12M 27/06* (2013.01); *C12M 27/18* (2013.01); *C12M 41/24* (2013.01); *Y02E 50/343* (2013.01)

(56) References Cited

FOREIGN PATENT DOCUMENTS

| | | |
|---|---|---|
| DE | 102009002925 A1 | 11/2010 |
| DE | 102009041569 A1 | 4/2011 |
| EP | 0025571 A1 | 3/1981 |
| EP | 1130336 A2 | 9/2001 |
| EP | 2602020 A2 | 6/2013 |
| EP | 2628958 A2 | 8/2013 |
| WO | 2009040330 A2 | 4/2009 |
| WO | 2014033075 A1 | 3/2014 |

OTHER PUBLICATIONS

International Search Report for PCT/EP2015/074493, dated May 12, 2016, 3 pages.

TEMPERATURE CONTROL APPARATUS

CROSS-REFERENCE TO RELATED APPLICATIONS

This patent application is a U.S. National Phase Patent Application of PCT Application No. PCT/EP2015/074493, filed Oct. 22, 2015, which claims priority to German Patent Application No. 102014016297.4, filed Nov. 6, 2014, each of which is incorporated by reference herein in its entirety.

FIELD OF THE INVENTION

The present invention relates to a tempering device for tempering of biomass contained in a container, and a biogas plant for production of biogas by microbial conversion of pumpable biomass.

BACKGROUND OF THE INVENTION

In biogas plants, bacteria are responsible for the decomposition and conversion of biomass into biogas. The bacteria have optimum living conditions only at a specific temperature at which the biochemical process proceeds effectively. For microbial conversion of biomass into biogas, therefore, it is necessary to keep the temperature in the septic tank constant. In mesophilic operation, the temperature lies ideally between around 35° C. and 40° C. Also, the biomass contained in the septic tank must be circulated in order to supply the bacteria with fresh nutrients.

Conventionally, cylindrical or flat heating bodies made from tubes with warm water flow are used as heat exchangers for heating the biomass in septic tanks. For example, German publication 28 21 790 or JP 3 161039 A describe heating bodies which heat the biomass in cooperation with agitators, so that the biomass is tempered as evenly and effectively as possible.

DE 10 2009 002 925 A1 discloses a heating and agitation register in which the heating register is positioned relative to an agitator such that a flow generated by the agitator can pass at least partially through and around the heating register. The heating register and the agitator here form a unit which can be inserted as one element into the septic tank. It is an advantage here that, on installation of the combined assembly, there is no need to ensure a suitable spacing between the agitator and heating register, and installation in a filled septic tank is possible. The heating register is made from tubes which are arranged in a plane transversely to the flow direction of the biomass, in order to enlarge the heat transfer area. One disadvantage of the heating register used here is that the intermediate spaces through which the biomass flows have a limited free cross-section on which undesirable deposits or temporary blockages can form.

SUMMARY OF THE INVENTION

The invention is based on the object of specifying a tempering device which tempers biomass as evenly and effectively as possible, and which at the same time is configured such that deposits of biomass thereon can be prevented. A biogas plant is also indicated which comprises a tempering device with the desired properties.

This object is achieved by a tempering device for tempering of biomass contained in a container, and a biogas plant for production of biogas by microbial conversion of pumpable biomass.

Accordingly, a tempering device is provided for tempering of biomass contained in a container, comprising at least one tempering means and at least one conveying device for conveying a mass flow of biomass in a main flow direction, wherein the at least one conveying device comprises at least one agitator, and wherein the at least one tempering means is arranged in the main flow direction generated by the at least one conveying device, wherein the at least one tempering means is configured tubular with an inner tube and with an outer tube arranged coaxially to the inner tube, wherein the inner tube and the outer tube form an intermediate space through which a tempering medium may flow, and wherein the at least one tempering means is oriented relative to the at least one conveying device such that, in operation of the tempering means, preferably at least 40% of the delivery volume of the mass flow generated by the at least one conveying device flows through the inner tube. The agitator moves the biomass through the tubular heat exchanger. The tubular structure is advantageous since the surface is oriented substantially parallel to the flow direction of the biomass, and thus deposits and blockages can be prevented. Furthermore, the tubular structure offers a large contact surface via which the biomass is tempered. The targeted flow generated by the agitator increases the through-flow of biomass at the heat exchanger, which leads to an even temperature distribution of the biomass in the container.

Preferably, it is provided that more than 75% of the delivery volume of the mass flow generated by the at least one conveying device flows through the inner tube. Here it is advantageous if even more than 90% of the delivery volume of the mass flow generated by the at least one conveying device flows through the inner tube.

It is also advantageous if the at least one tempering means is arranged downstream of the at least one conveying device and is oriented such that the longitudinal axis of the at least one tempering means coincides with a rotational axis of the at least one agitator.

In one embodiment, the at least one tempering means is a heat exchanger.

In one embodiment, the conveying device is dimensioned such that a diameter of an envelope of the at least one conveying device lies in a range between 100 and 140% of the inner diameter of the inner tube of the at least one tempering means. In this way, it can be guaranteed that a part of the mass flow passes through the inner tube and the other part along the outside of the at least one tempering means.

In another embodiment, it is provided that the at least one conveying device is dimensioned such that it is arranged in the inner tube of the at least one tempering means.

In one embodiment, it is provided that the at least one conveying device is a single agitator.

In order to keep the tempering device as compact as possible, it has a holding device comprising a foot, wherein the foot is configured to erect the tempering device on a floor of a container, and wherein the at least one conveying device and the at least one tempering means are held on the holding device. The holding device may be fixedly installed in the container, but it may also be configured to be portable.

Preferably, the main flow direction generated by the at least one conveying device is oriented parallel to the foot.

Furthermore, a biogas plant is provided, with a container for receiving the biomass and with a tempering device for tempering the biomass contained in the container, with at least one of the above-mentioned properties.

Here, it is advantageous if the container is circular cylindrical and the tempering device is arranged in the container so that the main flow direction is oriented in the direction of the middle of the container, at an angle of 10 to 40° relative to the radius of the floor. With larger containers, a smaller angle is preferred in order to guarantee a good mixing and tempering. For even mixing of the biomass, preferably at least two further agitators may be provided in the container, which are arranged on a wall of the container and are distributed evenly over the container with the tempering device.

BRIEF DESCRIPTION OF THE DRAWINGS

An exemplary embodiment of the invention is described below with reference to the drawings. The drawings show.

DETAILED DESCRIPTION OF THE INVENTION

Figure 1:
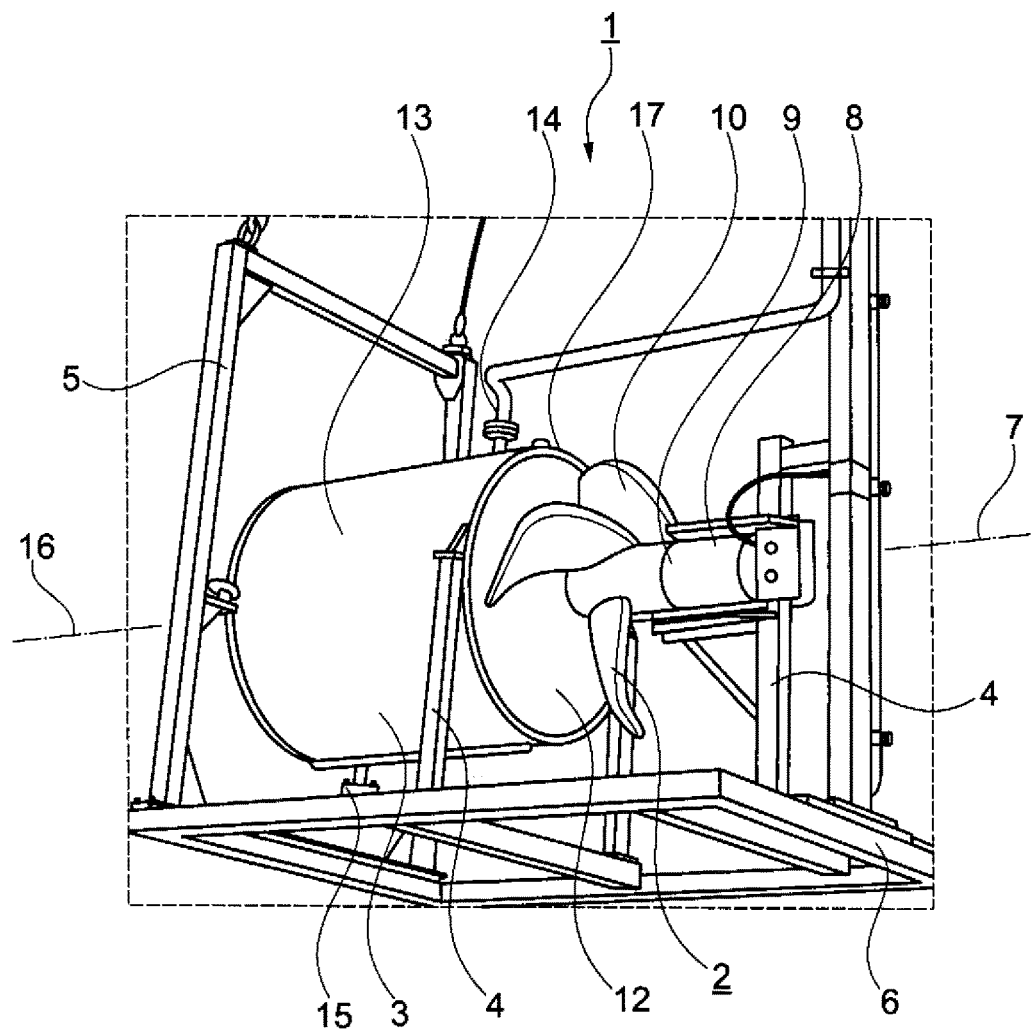
FIG. 1 a spatial view of a tempering device with an agitator.
Figure 2:
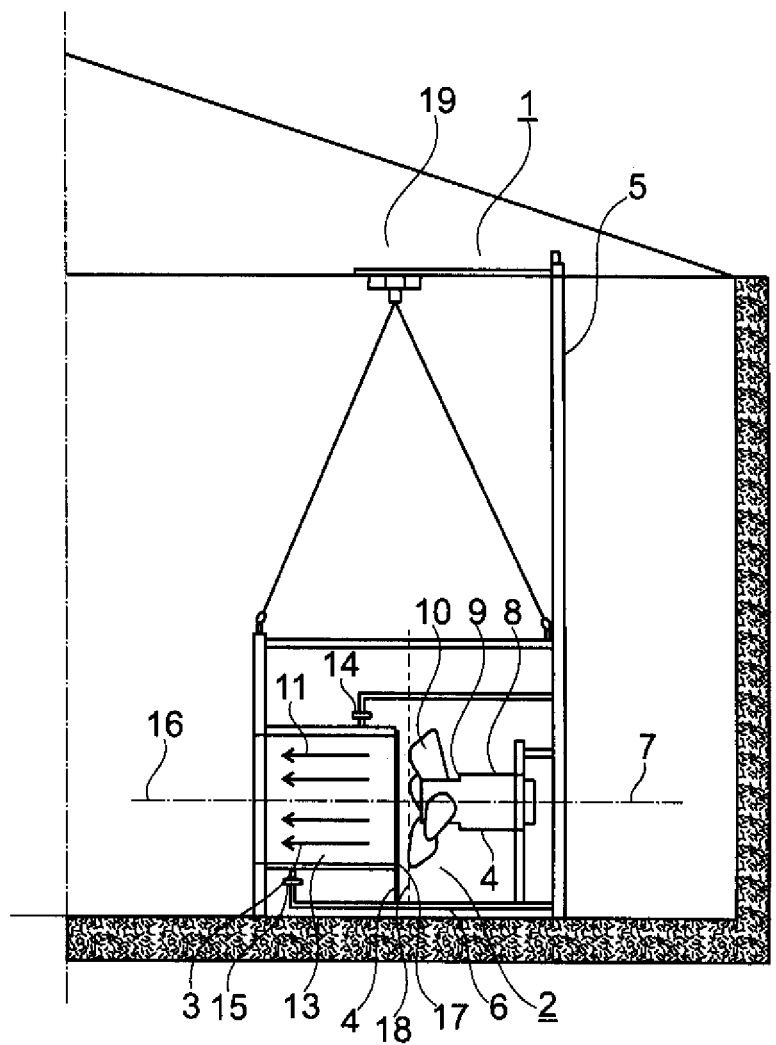
FIG. 2 a side view of a tempering device with an agitator.

FIGS. 1 and 2 show a tempering device 1 for containers of biogas plants, with an agitator 2 and a heat exchanger 3. The heat exchanger 3 and the agitator 2 are connected to a holding device 5 via carriers 4. The holding device 5 has a floor frame 6 (foot) for erection of the tempering device 1 on the floor of a container. The agitator 2 is arranged with its rotational axis 7 parallel to the floor frame 6. The agitator 2 is directly connected to a drive 8. The drive 8 is thus situated inside the container or biomass during operation of the tempering device. The agitator 2 has three agitator blades 10 mounted on an agitator shaft 9, which rotate about the rotational axis 7 when driven by the drive 8. The agitator blades 10 are configured such that the biomass is drawn in on the side close to the drive and the biomass is pushed away from the agitator 2 on the side remote from the drive. This gives a primarily axial main flow 11 of the biomass, oriented away from the drive 8. The heat exchanger 3 is arranged downstream of the agitator 2 on the side remote from the drive. The heat exchanger 3 is configured tubular with a double wall. The heat exchanger 3 has an inner tube 12 through which the biomass may flow, and an outer tube 13 arranged coaxially to a longitudinal axis. In operation, a tempering medium flows through the intermediate space formed between the inner tube 12 and the outer tube 13. The intermediate space is connected to a tempering medium discharge 14 in a region close to the agitator, and to a tempering medium supply 15 in a region remote from the agitator. The discharge 14 and supply 15 are thus arranged diametrically. The heat exchanger 3 is positioned such that its longitudinal axis 16 coincides with the rotational axis 7 of the agitator 2. The inner diameter of the heat exchanger 3 is slightly smaller than the diameter of the envelope of the agitator 2 or agitator blades 10. The heat exchanger 3 is preferably between 1 m and 3 m long. The heat exchanger 3 is arranged directly behind the agitator 2 in the flow direction 11. The distance between an end face 17 of the heat exchanger 3 close to the agitator and an outer end 18 of the agitator 2, formed by the agitator blades 10, lies in a range between 10 cm and 3 m.

The holding device 5 furthermore comprises a transport device 19 which, in operation, protrudes out of the biomass contained in the container. By means of the transport device 19, the tempering device 1 as a heat exchanger 3 and the component comprising the agitator 2 may be removed, relocated or inserted even when the container is filled with biomass, without an undesirable evacuation of the container being required.

Figure 3:
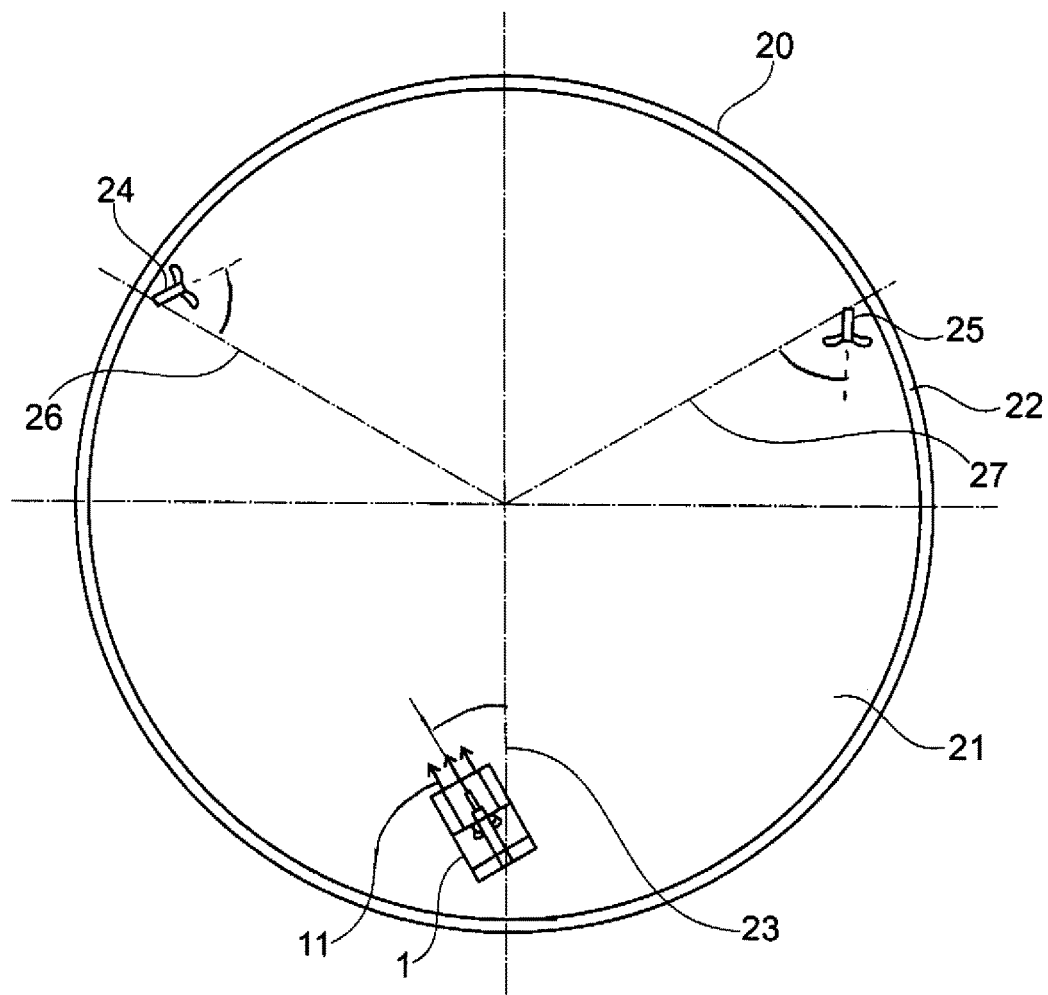
FIG. 3 a top view of a biogas plant with container and a tempering device arranged therein according to FIG. 1, and FIG. 4 a spatial view of a biogas plant with container and a tempering device arranged therein according to FIG. 1.
Figure 4:
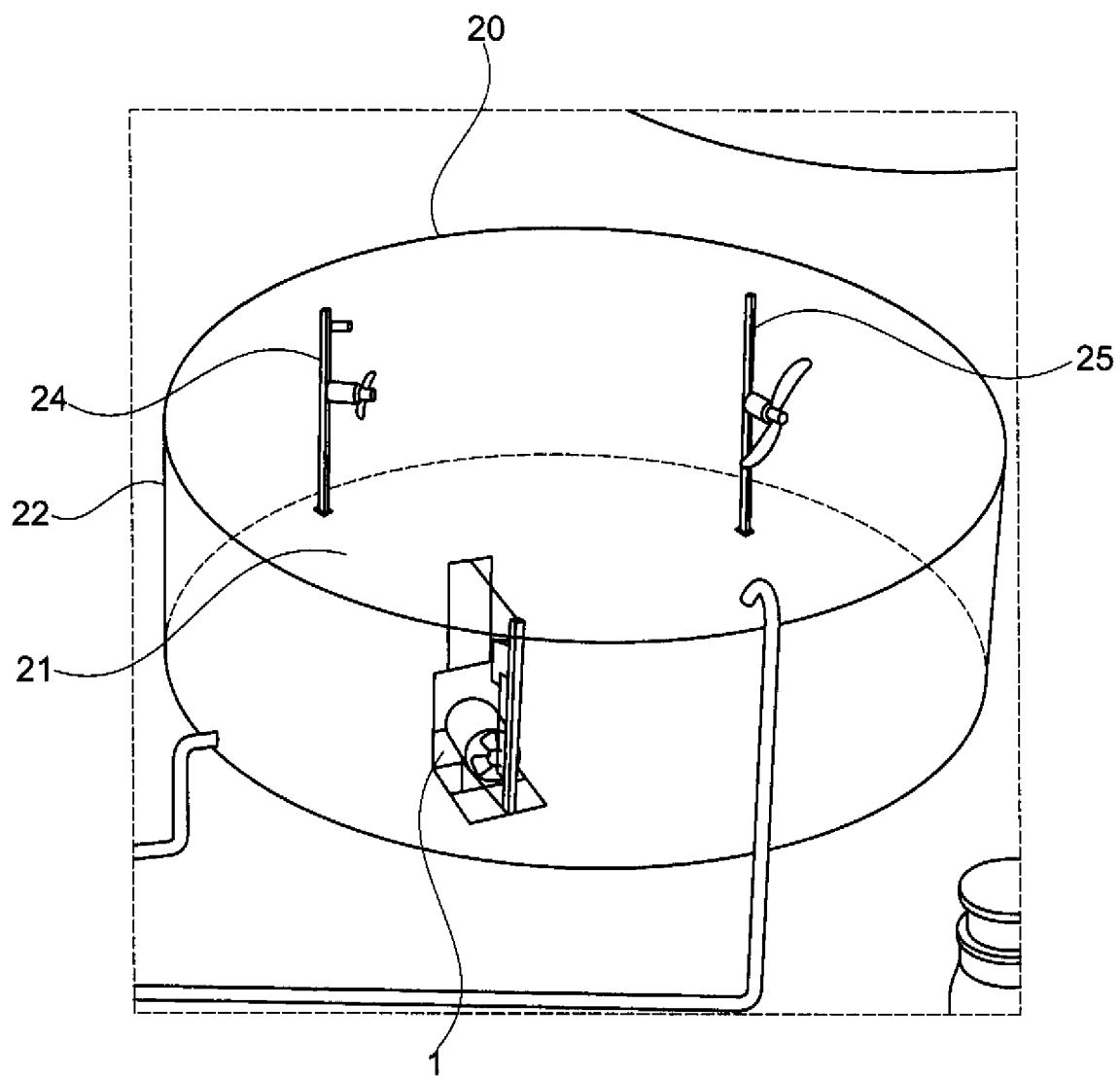

The tempering device 1 is arranged in a circular cylindrical container 20, preferably as shown in FIGS. 3 and 4. The container 20 has a circular floor 21 and a wall 22 arranged perpendicular thereto. The longitudinal axis 16 of the heat exchanger 3, or the rotational axis 7 of the agitator 2, is oriented at an angle of around 30° to the radius 23 of the floor 21 of the container 20, so that the agitator 2 moves the biomass away from the wall 22 towards the interior of the container 20. The distance from the wall 22 is ideally selected in an order of magnitude of 1 m to 3 m.

In order to achieve a good mixing of the biomass, two further agitators 24, 25 are provided. These two agitators 24, 25 are arranged on the inside of the wall 22 and oriented at an angle of 60° to the radius 26, 27 of the floor 21 of the container 20. The agitators 24, 25 are each arranged at an angle of 120° to the tempering device 1, starting from the centre point of the floor. The two agitators 24, 25 and the tempering device 1 are oriented such that they are each arranged in the flow direction and hence generate a main flow of approximately the same orientation in a peripheral direction of the circular floor.

In the view in FIG. 3, the agitators 24, 25, 2 are arranged such that a substantially clockwise flow is formed.

In operation, the heat exchanger emits heat to the biomass contained in the container. If the temperature rises too greatly during the conversion to biogas, the heat exchanger may also extract heat from the septic tank. Cooling of the biomass is thus also possible. Any suitable heat carrier, preferably water or thermal oils, may be used as a tempering medium. The agitator pushes the biomass through the tubular heat exchanger and past it on the outside. The tubular structure is advantageous since the surface is oriented substantially parallel to the flow direction of the biomass, and hence deposits and blockages can be prevented. Furthermore, the tubular structure offers a large contact surface via which the biomass is tempered. The targeted flow generated by the agitator increases the through-flow of biomass at the heat exchanger, which leads to an even temperature distribution of the biomass in the container.

It may also be provided that several agitators are arranged behind each other downstream, each with a heat exchanger.

The tempering device according to the invention may be installed in the combination fixedly in a container. It may, however, also be provided that the tempering device is configured to be portable so that the device may be removed from the container, for example for maintenance or exchange.

Depending on the area of application, the tempering device may be installed in the container horizontally or vertically. For example, with circular cylindrical or lying tank-shaped containers (e.g. fermenters), a horizontal orientation is desirable. However, in standing tank-shaped containers, a vertical orientation of the tempering device is preferred.

The agitator is preferably configured as an axially conveying agitator with two to four agitator blades. The agitator blades are curved, whereby the highest possible speed of the biomass is achieved with a slow running agitator, and hence optimal mixing.

In large containers, it may be provided that the tempering device has a tube which adjoins the at least one tempering means downstream in the flow direction. Here it is preferred if the tube has approximately the same inner diameter as the at least one tempering means, and the conveyor device or agitator is arranged inside the heat exchanger. This embodiment of the tempering device according to the invention ensures a tempering and mixing of the biomass with a large action radius. Since 100% of the mass flow generated by the agitator flows through the heat exchanger and the tube placed thereon, and a back flow forms outside the tube, remote regions of the container can also be agitated.

The tempering device according to the invention may be used amongst others in septic tanks or fermenters, hydrolysis fermenters and secondary fermentation containers of biogas plants, and containers of sewage plants. The tempering device is designed such that the biomass can be tempered evenly and effectively, and deposits of biomass on the outside are prevented.

The invention claimed is:

1. A tempering device for tempering of biomass contained in a container, the tempering device comprising:
 - at least one conveying device comprising at least one agitator for conveying a mass flow of biomass in a main flow direction, and
 - at least one tempering means arranged in the main flow direction generated by the at least one conveying device, wherein the at least one tempering means is tubular and includes an inner tube and an outer tube arranged coaxially to the inner tube,
 - wherein the at least one conveying device is positioned outside of the inner tube of the tempering means to deliver fluid both through the inner tube and over the outer tube,
 - wherein an intermediate space is disposed between the inner tube and the outer tube through which a tempering medium may flow,
 - wherein the at least one tempering means is oriented relative to the at least one conveying device such that at least 40% of a delivery volume of the mass flow generated by the at least one conveying device flows through the inner tube,
 - wherein the at least one tempering means is arranged downstream of the at least one conveying device and is oriented such that a longitudinal axis of the at least one tempering means coincides with a rotational axis of the at least one agitator, and
 - wherein a diameter of an envelope of the at least one conveying device lies in a range between 100% and 140% of an inner diameter of the inner tube of the at least one tempering means.

2. The tempering device according to claim 1, wherein more than 75% of the delivery volume of the mass flow generated by the at least one conveying device flows through the inner tube.

3. The tempering device according to claim 1, wherein more than 90% of the delivery volume of the mass flow generated by the at least one conveying device flows through the inner tube.

4. The tempering device according to claim 1, wherein the at least one tempering means is a heat exchanger.

5. The tempering device according to claim 1, wherein the at least one conveying device is a single agitator.

6. The tempering device according to claim 1, wherein the tempering device includes a holding device comprising a foot, wherein the foot is configured to erect the tempering device on a floor of a container, and wherein the at least one conveying device and the at least one tempering means are held on the holding device.

7. The tempering device according to claim 6, wherein the main flow direction generated by the at least one conveying device is oriented parallel to the foot.

* * * * *